US00PP12639P2

(12) United States Plant Patent
Arndt

(10) Patent No.: US PP12,639 P2
(45) Date of Patent: May 21, 2002

(54) PHALAENOPSIS ORCHID PLANT NAMED 'ANTHURA GOLD'

(75) Inventor: Gunter Arndt, Burlo (DE)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 09/549,535

(22) Filed: Apr. 14, 2000

(51) Int. Cl.[7] ..... A01H 5/00
(52) U.S. Cl. ..... Plt./311
(58) Field of Search ..... Plt./311

(56) References Cited

U.S. PATENT DOCUMENTS

PP4,715 P * 5/1981 Guo ..... Plt./311

OTHER PUBLICATIONS

Anthura catalogue, Bleiswijk, Holland (1998/1999).

* cited by examiner

*Primary Examiner*—Bruce R. Campell
*Assistant Examiner*—Susan B. McCormick
(74) *Attorney, Agent, or Firm*—Foley & Lardner

(57) ABSTRACT

A new and distinct Phalaenopsis orchid plant named 'Anthura Gold' particularly characterized by its attractive and unique yellow flowers and economical propagation via tissue culture. 'Anthura Gold' has relatively small, dark-green foliage, a rapid growth rate, and a compact plant structure which is suitable for packaging and shipping to the market.

3 Drawing Sheets

BACKGROUND OF THE INVENTION

The present invention comprises a new and distinctive cultivar of orchid plant, botanically known as Phalaenopsis and hereinafter referred to by the cultivar name 'Anthura Gold'. The genus Phalaenopsis is a member of the family Orchidaceae.

Phalaenopsis comprises a genus of about 55 species of herbaceous perennials many of which, or the hybrids thereof, are suitable for cultivation in the home or greenhouse. Phalaenopsis is prodominantly epiphytic or rock-dwelling, and is native to tropical Asia, Malay Archipelago and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

Phalaenopsis orchids, often referred to as 'Moth Orchids' in the horticultural trade, are frequently used to furnish cut flowers for the florist trade or sold as flowering potted-plants for home or interiorscape.

Phalaenopsis produces upright or pendent lateral racemes, often with many showy flowers which open in succession beginning with the lowermost. The flowers possess three sepals and three petals; the lateral ones being alike. The lowermost petal, called the labelum, is three-lobed and is often more brightly-colored than the other flower segments. Flower colors include various shades of pink, white, yellow and red-brown.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate.

'Anthura Gold' is particularly characterized by its attractive and unique yellow flowers, economical propagation via tissue culture, rapid growth, and a plant dimension suitable for packaging and shipping to the market.

'Anthura Gold' is a product of a planned breeding program which had the objective of creating new orchid cultivars having yellow flowers and a compact plant sutucture.

The new cultivar was originated from a hybridization made in a controlled breeding program in Burlo, Germany in 1992. 'Anthura Gold' is a result of a cross of selected, but unnamed, Phalaenopsis cultivars. 'Anthura Gold' was discovered and selected as one flowering plant within the progeny of the stated cross by the inventor, Gunter Arndt, in 1992 in a controlled environment in Burlo, Germany.

The first act of asexual reproduction of 'Anthura Gold' by tissue culture was performed by the inventor in a controlled environment in Merelbeke, Belgium in 1994. Horticultural examination of selected units initiated in 1998 has demonstrated that the combination of characteristics as here in disclosed for 'Anthura Gold' are firmly fixed and are retained through successive generations of asexual reproduction.

BRIEF DESCRIPTION OF THE INVENTION

The following traits have been repeatedly observed and determined to be basic characteristics of 'Anthura Gold' which in combination distinguish this orchid as a new and distinct cultivar:

1. flowers which are light-yellow in color;
2. plant produces more than one inflorescence, in contrast to most other Phalaenopsis cultivars;
3. inflorescence is short and sturdy;
4. relatively small, dark-green foliage;
5. compact structure, therefore easy to process and package for shipping; and
6. plants may be propagated economically and uniformly using tissue culture.

'Anthura Gold' has not been observed under all possible environmental conditions. The phenotype may vary significantly with variations in environment such as temperature, light intensity, fertilization and daylength without any change in the genotype. The following obervations, and measurements describe plants grown in Burlo, Germany under conditions, which approximate those generally used in commercial practice.

Presently, there is no commercial cultivar to which 'Anthura Gold' can be meaningfully compared.

BRIEF DESCRIPTION OF THE DRAWINGS

The accompanied photographic illustrations show typical plant and flower characteristics of 'Anthura Gold' with colors being as true as possible with illustrations of this type.

Sheet 1 is a side view of a plant of 'Anthura Gold'.

Sheet 2 is a close-up view showing the characteristics of the flower.

Sheet 3 is a close-up view showing the characteristics of the leaf.

DETAILED BOTANICAL DESCRIPTION

In the following description, color references are made to The Royal Horticultural Society (R.H.S.) Colour Chart. The color values were determined between 11:00 a.m. and 1:00 p.m. on Oct. 20, 1999, under 10,000 lux natural light in a glasshouse at Bleiswijk, The Netherlands.

The age of the observed plant is 75 weeks from planting.

Origin: Seedling from a cross of selected but unnamed parentage.

Classification: Phalaenopsis hybrid cv. 'Anthura Gold'.

Propagation: Asexual propagation by tissue culture.

Plant:

*Size.*—A mature plant has a height of approximately 30 cm. Under apprppriate growing conditions, plants obtain a mature size of approximately 50 in height for a mature plant and approximately 25 cm14 30 cm in width.

*Growth habit.*—Compact, small, dark-green leaves and a relatively short raceme.

*Vigor.*—26 weeks after planting from tissue culture, 2 leaves appear; at 30 weeks, 3–4 leaves appear; after a cold treatment of 4–8 weeks at a temperature of 19° C., 1 to 4 branches with flowers appear.

*Flowers per stem.*—Approximately 10 to 12.

*Stems.*—1–4 stems present, green RHS 146A to 146B, fleshy; approximately 30–40 cm in length, approximately 0.4–0.6 in diameter. Internode length approximately 1 cm.

Foliage:

*Quantity.*—Approximately 6 to 8 leaves are produced before flowering.

*Size of leaf.*—13 to 16 cm long and 6 to 8 cm wide.

*Shape.*—The leaf blade is short and elliptic with a cuneate base and an obtuse tip. The leaf blade is leathery and thick. The midvein protrudes, while the other veins are sunken in the thick leaf blade and therefore not visible.

*Arrangement.*—Horizontal and on two sides parallel.

*Color.*—Upper surface: Dark-green, RHS 147A. Lower surface: Light-green, RHS 146A–B with a dark-green leaf margin, RHS 147A.

*Leaf blade.*—Form: The leaf blade is short ovate with an obtuse tip and a cuneate base. The margins are entire. The midrub is straight over the length of the leaf. The leaf blade is flat or slightly folded upward from the midrib. The upper leaf side is slightly glossy. The leaves are leathery and thick. Size: Leaf blades of a mature-sized plant are approximately 13 cm14 16 cm in length and approximately 6 cm to 8 cm in width. Veins: Veins are sunken within the thick leaf blade, veination pattern cannot be observed due to the dark green leaf color. Color: Adaxial surface: Darker and greener than, but closest to RHS 137A. Abaxial surface: RHS 143A.

Inflorescence:

*Description.*—The sepals and petals are light-yellow in color. There are 2 petals which are fleshy and glabrous in texture, with margins weakly undulate. There are 3 sepals which are fleshy and glabrous in texture, with straight margins. The lateral (lower) sepals have very small, dark speckles at the base. The sepals are elliptic-ovate in shape and the petals are broadly-ovate. The sepals and petals are weakly cupped. The labellum is three-lobed with two prominent callosities at the central junction of the lateral lobes and base of the midlobe. The lateral lobes of the labellum fold upward about the column; the midlobe extends forward and is terminated by two short filiform appendages at the apex. The lateral lobes of the labellum are obovate in shape while the midlobe is triangular. The labellum is yellow in base color with small orange spots in the center part. The two callosities are orange. The margins of the labellum are yellow.

*Dimensions.*—Overall: Approximately 5.8 cm to 6.2 cm wide, and 5.8 cm to 6.0 cm in height. Sepals: Approximately 3.1 cm to 3.3 cm long and 2.3 cm to 2.5 cm wide. Petals: Approximately 3.0 cm to 3.2 cm long and 2.5 cm to 2.7 cm wide. Labellum: Approximately 2.5 cm to 2.7 cm long and 1.6 cm to 1.7 cm wide (not flattened).

*Color.*—Sepals: Adaxial and abaxial surfaces are light-yellow, RHS 2D. Petals: The adaxial and abaxial surfaces of the mid-petal are light-yellow, RHS 2D. The adaxial and abaxial surfaces of the lateral petals are RHS 2D, with the adaxial-surfaces, small speckles, RHS 22A–B, at the base. Labellum: The base color of the adaxial and abaxial surfaces are light-yellow, RHS 12B, with a dark yellow center part, RHS 22A–B. Callosities: Main color is RHS 22A–B. As the flower ages, the color of the labellum becomes darker-yellow to orange-yellow, RHS 21B.

*Raceme.*—Dimension: The raceme is approximately 30 to 35 cm from base to tip, and 0.5 cm in diameter at the midpoint. The color of the raceme is RHS 146A.

*Flowering time.*—For an untreated plant (flowering plant that has not undergone cold-treatment where the plant grows at a temperature of 18–19° C. during 4–8 weeks after a period of 30 weeks at a temperature of 25° C.), as depicted in the photograph of the full plant, two racemes appear at the same time with 20 to 25 flowers/unopened buds. First flowers can be expected approximately 4–6 months after planting a plant with a leaf diameter of 3 to 5 cm.

*Lastingness of flowers.*—On the plant is 4–6 months, lastingness of cut flowers has not been observed.

*Fragrance.*—No fragrance.

Reproductive organs: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Approximately 9 to 10 mm long and 6 to 7 mm wide, RHS 155A.

*Pollinia*.—Two, 1 mm oval masses of pollen present, RHS 23A.

*Ovary*.—9 to 11 mm long and 3 mm in diameter, RHS 145A.

*Pedicel*.—Aproximately 3.5 cm long and 3 mm in diameter, RHS 145A.

Roots: Fleshy, approximately 5 mm–7 mm wide and green, RHS 146C–D. It takes 12 weeks for plants growing in tissue culture to initiate roots.

Plant disease resistance/susceptibility: No specific resistance or susceptibility observed.

General observations: Phalaenopsis 'Anthura Gold' produces two or more inflorescence with flowers having light-yellow sepals and petals, an orange-yellow labellum and a white column. The inflorescence is strong, relatively short, and easily packaged for shipping. The plant grows very quickly to marketable size. 'Anthura Gold' can be economically propagated via tissue culture.

I claim:

1. A new and distinct cultivar of Phalaenopsis orchid plant named 'Anthura Gold' as illustrated and described.

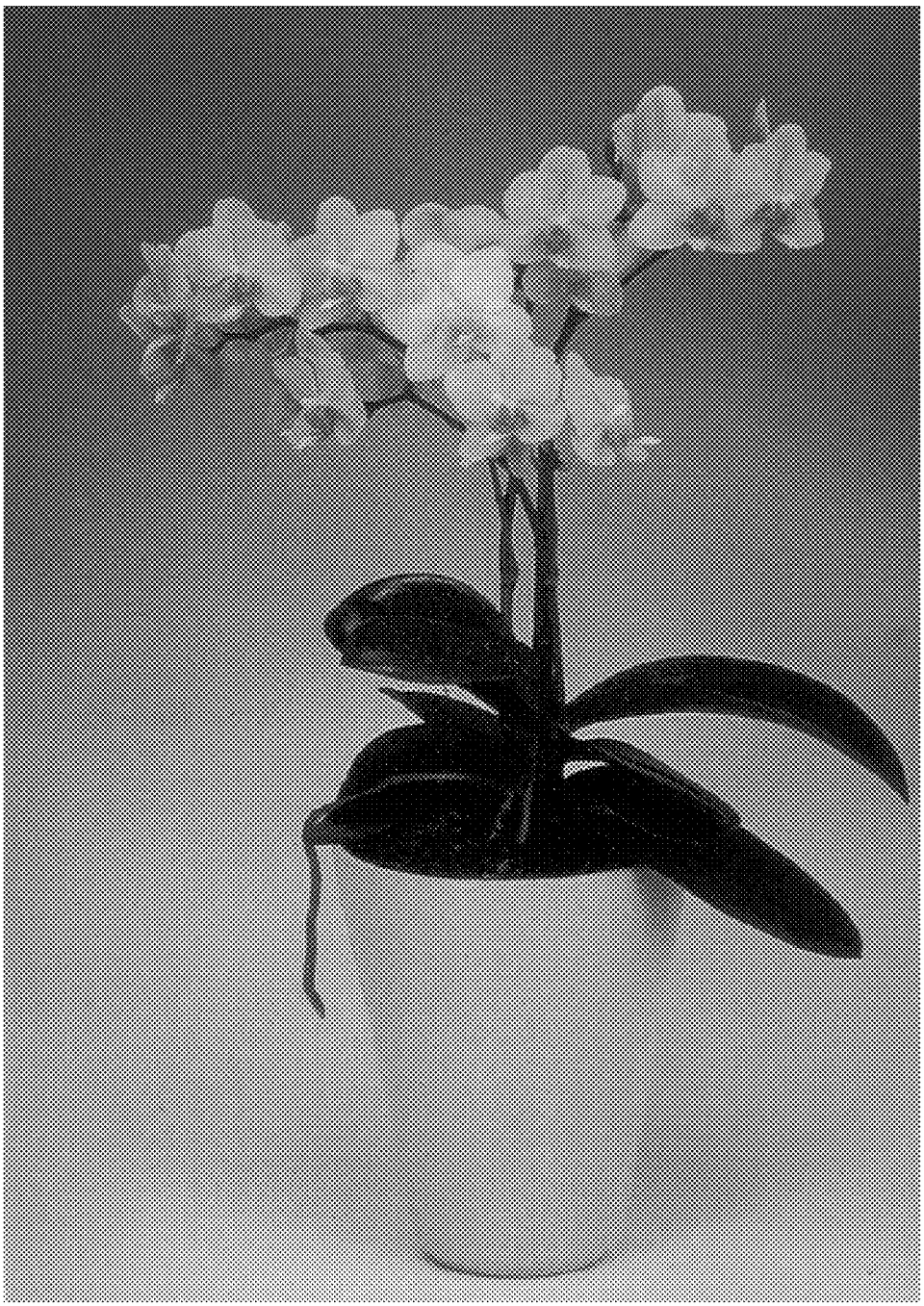

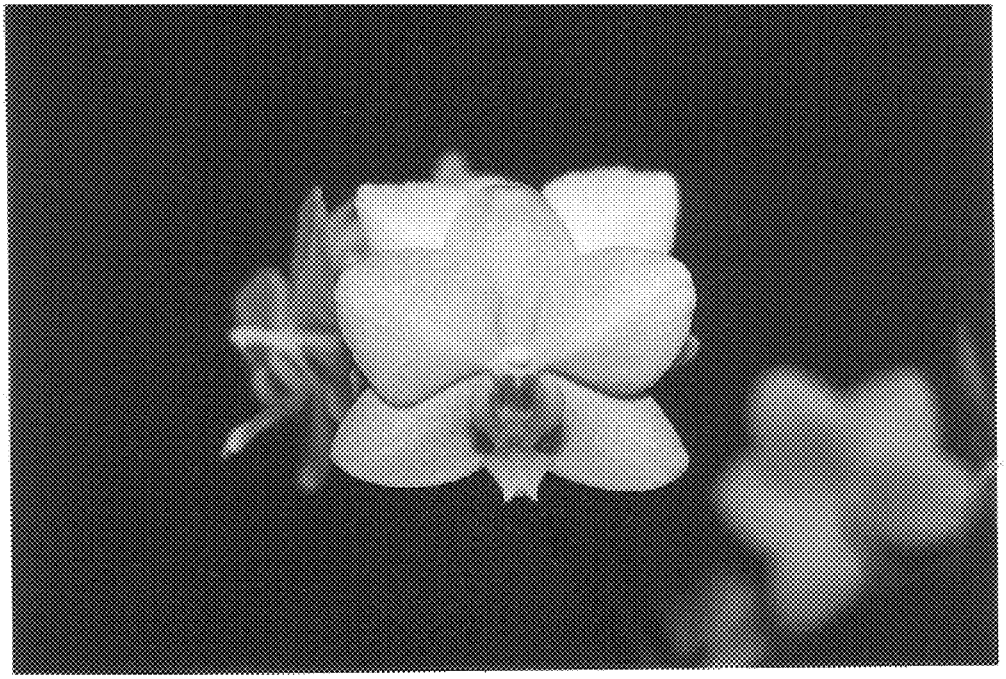

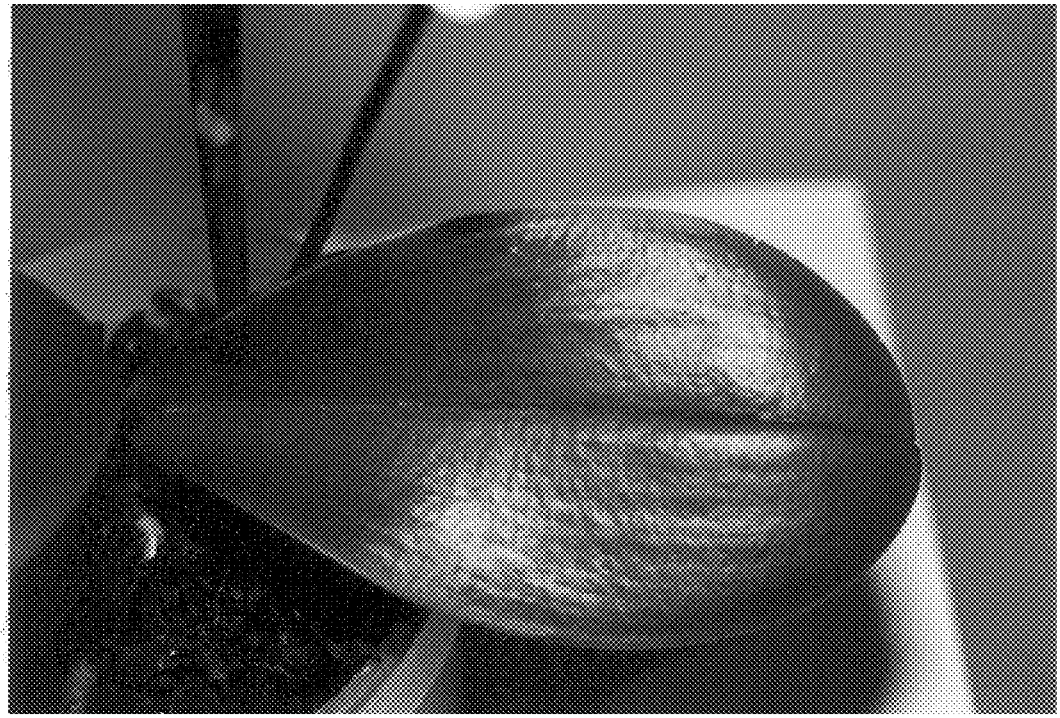

* * * * *